United States Patent [19]
McGee et al.

[11] Patent Number: 5,860,920
[45] Date of Patent: Jan. 19, 1999

[54] SYSTEMS FOR LOCATING AND ABLATING ACCESSORY PATHWAYS IN THE HEART

[75] Inventors: David L. McGee, Palo Alto; Russell A. Houser, Livermore; David K. Swanson, Mountain View, all of Calif.

[73] Assignee: EP Technologies, Inc., San Jose, Calif.

[21] Appl. No.: 931,229

[22] Filed: Sep. 16, 1997

Related U.S. Application Data

[63] Continuation of Ser. No. 744,560, Nov. 6, 1996, Pat. No. 5,673,695, which is a continuation of Ser. No. 632,920, Apr. 16, 1996, abandoned, which is a continuation of Ser. No. 510,143, Aug. 2, 1995, abandoned, which is a division of Ser. No. 138,452, Oct. 15, 1993, abandoned.

[51] Int. Cl.$^6$ .............................. A61B 5/04; A61N 1/05
[52] U.S. Cl. ......................... 600/374; 600/509; 607/122; 606/41
[58] Field of Search ...................... 600/373, 375, 600/509, 516, 523; 607/116, 118, 119, 122, 123, 125, 128, 101, 102, 148, 154; 606/27, 32, 33, 41, 42

[56] References Cited

U.S. PATENT DOCUMENTS

| | | |
|---|---|---|
| 4,776,349 | 10/1988 | Nashef et a. . |
| 4,777,955 | 10/1988 | Brayton et al. . |
| 4,940,064 | 7/1990 | Desai . |

(List continued on next page.)

FOREIGN PATENT DOCUMENTS 880410  11/1981  Russian Federation .

OTHER PUBLICATIONS

Josephson et al., "Role of Catheter Mapping in the Preoperative Evaluation of Ventricular Tachycardia," *The American Journal of Cardiology*, vol. 49, Jan. 1982, pp. 207–220.

Calkins et al., "Electrogram Criteria for the Identification of Appropriate Target Sites for Radiofrequency Catheter Ablation of Accessory Atrioventricular Connections," *Circulation*, vol. 85, No. 2, Feb. 1992, pp. 565–573.

Desai, et al., "Two–Phase Radiofrequency Catheter Ablation of Isolated Ventricular Endomyocardium," *PACE*, vol. 14, Jul., 1991, pp. 1179–1194.

Yee, et al., "Tachycardia Associated with Accessory Atrioventricular Pathways," *Mechanisms of Clinical Arrhythmias*, Part VII, Chapter 51, pp. 463–472.

Prystowski et al., "Pre–excited Tachycardias," *Mechanisms of Clinical Arrhythmias*, Part VII, Chapter 52, pp. 472–479.

Gallagher et al., "Variants of Pre–excitation, Update 1989," *Mechanisms of Clinical Arrhythmias*, Part VIII, Chapter 53, pp. 480–490.

(List continued on next page.)

*Primary Examiner*—Jeffrey R. Jastrzab
*Attorney, Agent, or Firm*—Henricks, Slavin & Holmes LLP

[57] ABSTRACT

Systems and methods sense electrical events about a selected annulus region of the heart to identify the location of an accessory pathway. The systems and methods establish a contact site between heart tissue along the selected annulus and a multi-electrode array having a generally circular shape that conforms to the circumferential geometry of the selected annulus region. The systems and methods maintain the site of contact between the electrode array and heart tissue, while conveying signals representing electrical events sensed by bipolar pairs of the electrodes in the selected annulus region, The systems and methods display the signals as graphic information that represents the time differences between the atrial and ventricular electrogram complexes sensed by bipolar pairs of the electrodes on the selected annulus region. The bipolar pair of electrodes displaying the least time separation between the atrial and ventricular complexes identifies the region of the accessory pathway. With this information, the systems and methods convey energy to one or more of the electrodes of the selected pair to ablate tissue in the selected annulus region.

6 Claims, 8 Drawing Sheets

U.S. PATENT DOCUMENTS

| | | |
|---|---|---|
| 5,228,442 | 7/1993 | Imran . |
| 5,263,493 | 11/1993 | Avitall . |
| 5,275,162 | 1/1994 | Edwards et al. . |
| 5,354,297 | 10/1994 | Avitall . |
| 5,358,479 | 10/1994 | Wilson . |
| 5,362,926 | 11/1994 | Fukuda et al. . |

OTHER PUBLICATIONS

Jackman et al., "Catheter Recordings of Accessory Atrioventricular Pathway Activation," *Mechanisms of Clinical Arrhythmias*, Part VII, Chapter 54, pp. 491–502.

Kuck, et al., "Sites of Conduction Block in Accessory Atrioventricular Pathways; Basis for Concealed Accessory Pathways," *Mechanisms of Clinical Arrhythmias*, Part VIII, Chapter 55, pp. 503–511.

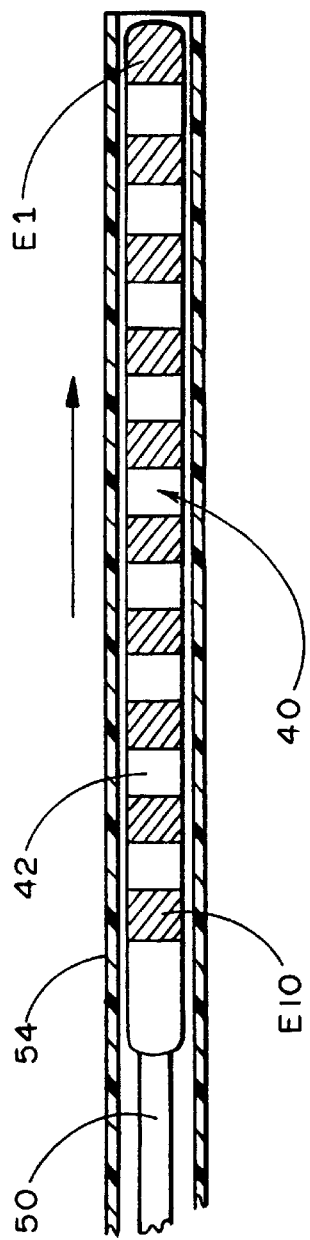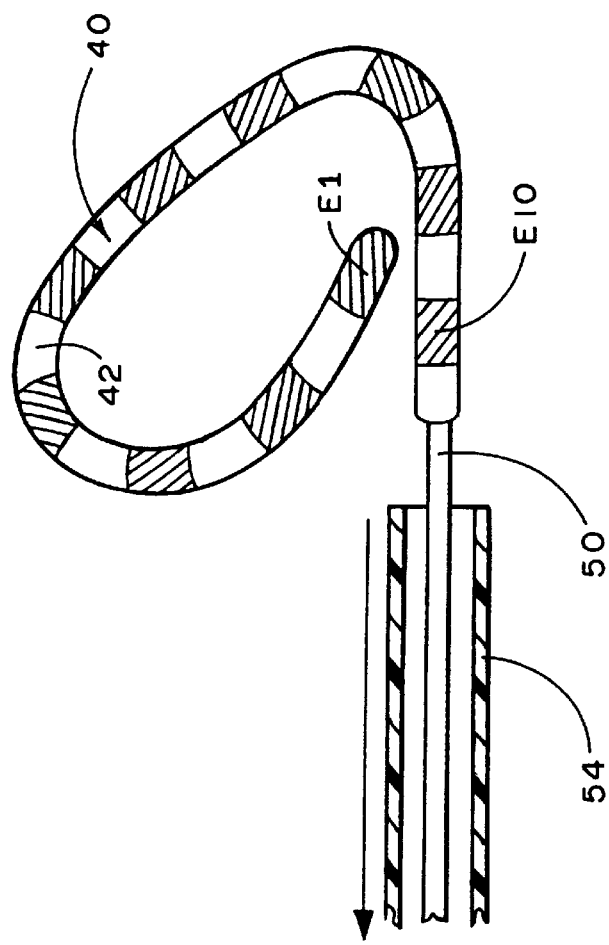

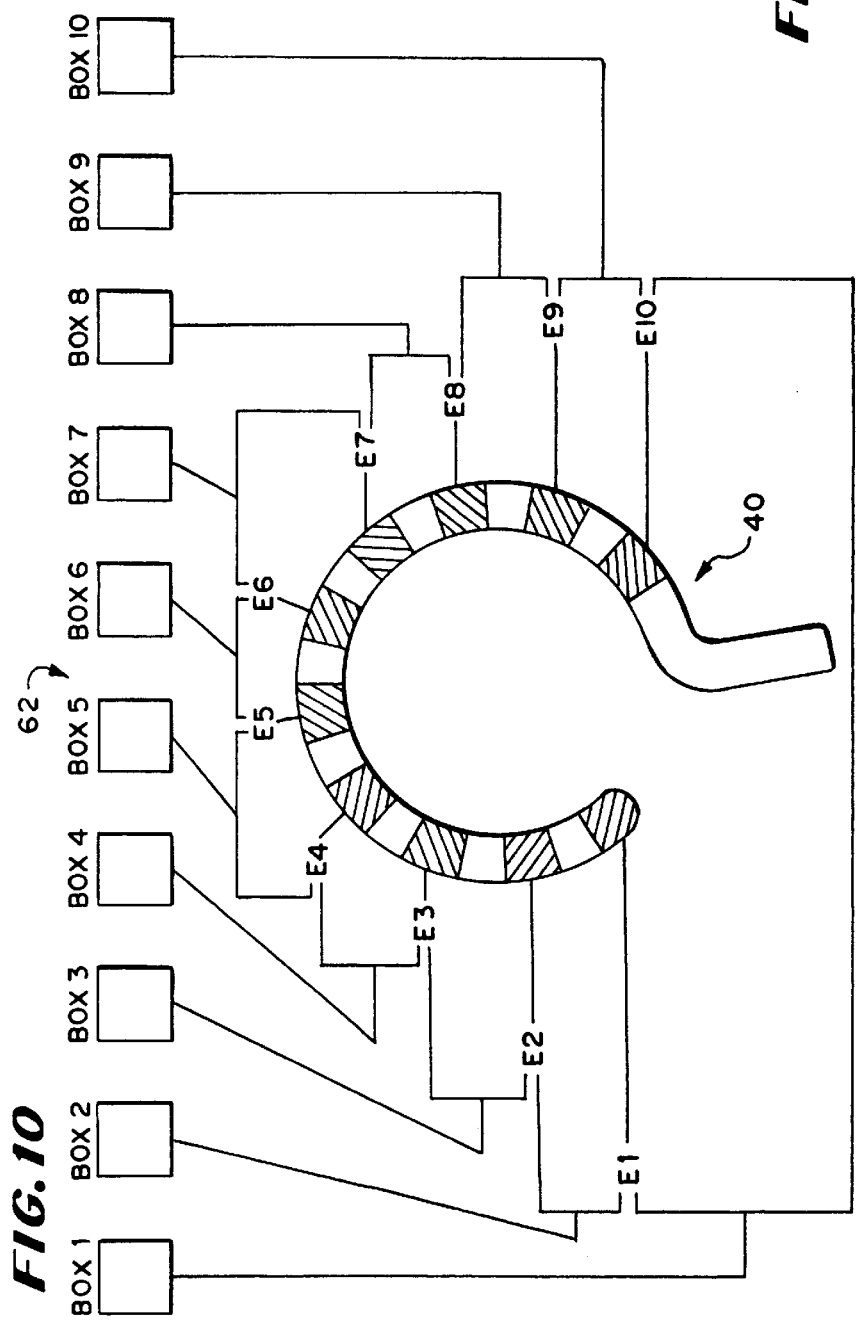
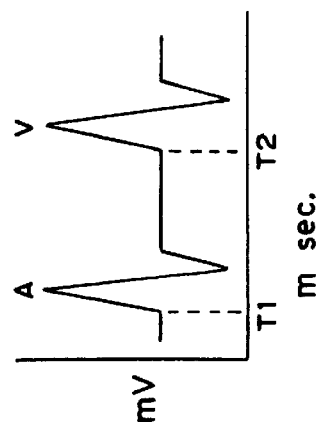
FIG.10
FIG.11

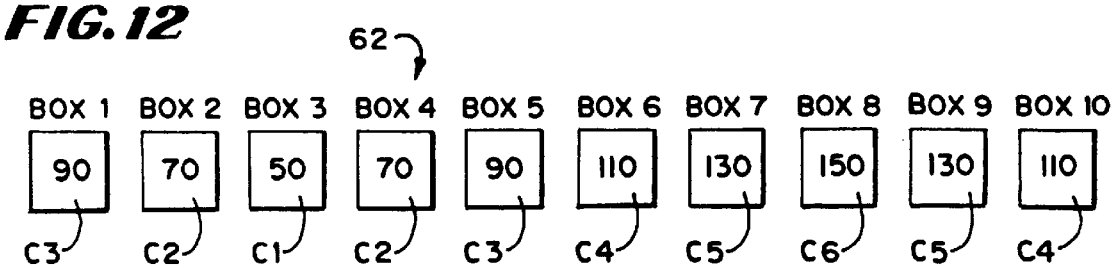
FIG. 12
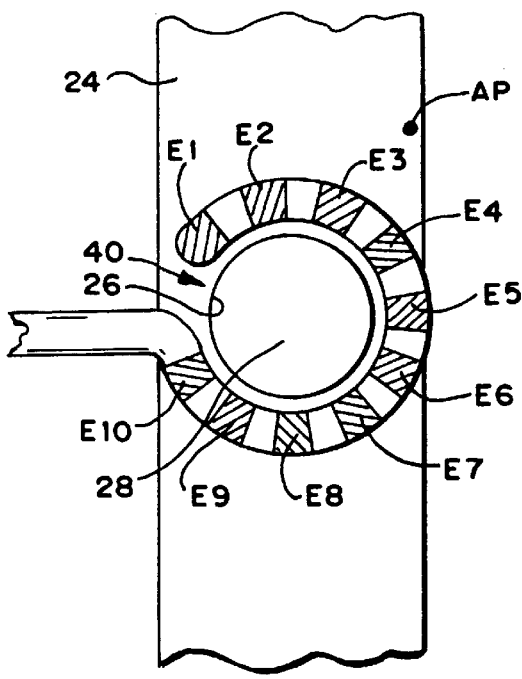
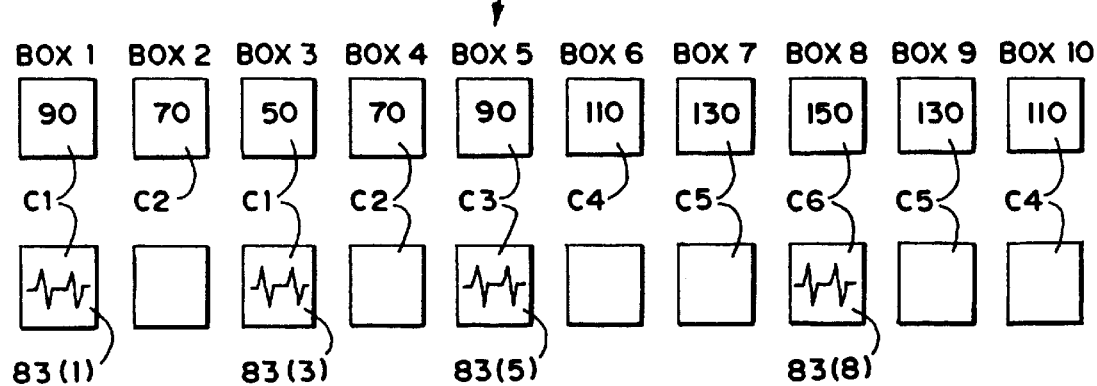
FIG. 13

SYSTEMS FOR LOCATING AND ABLATING ACCESSORY PATHWAYS IN THE HEART

This application is a continuation of application Ser. No. 08/744,560, now U.S. Pat. No. 5,673,695 filed on Nov. 6, 1996, which is a continuation of application Ser. No. 08/632,920, now abandoned, filed Apr. 16, 1996, which is a continuation of Ser. No. 08/510,143 filed on Aug. 2, 1995, now abandoned which is a divisional of application Ser. No. 08/138,452 filed on Oct. 15, 1993, which is now abandoned.

FIELD OF THE INVENTION

The invention is directed to systems and methods for mapping and ablating the interior regions of the heart for treating cardiac conditions.

BACKGROUND OF THE INVENTION

Normal sinus rhythm of the heart begins with the sinoatrial node (or "SA node") generating an electrical impulse. The impulse usually propagates uniformly across the right and left atria and the atrial septum to the atrioventricular (AV) groove. This propagation causes the atria to contract.

At the atrioventricular (AV) groove, the impulse encounters the so-called "skeleton" of the heart. Here, a fibrous structure separates the atria from the ventricles. The rings or annuli of the tricuspid valve (between the right atrium and right ventricle) and the mitral (or bicuspid) valve (between the left atrium and the left ventricle) are attached to this fibrous skeleton.

The fibrous skeleton is electrically inert. It normally acts as an insulator to block the conduction of the impulse from the SA node. The electrical impulse would be prevented from crossing over to the ventricular side of the AV groove, if not for the specialized AV conducting tissue, called the atrioventricular node (or "AV node") and the bundle of HIS (or "HIS bundle").

The AV node slows the conduction of the impulse to the ventricles, allowing the atria to first complete their contraction and empties blood from the atria into the ventricles. The slowed impulse eventually enters the HIS bundle, which delivers the impulse to the ventricular side. The ventricles then contract.

The AV conduction system results in the described, organized sequence of myocardial contraction.

Normally, the AV conduction system is the only way for electrical impulses to be conducted from the atria to the ventricles. However, some people are born with additional electrical conduction paths between the atria and ventricles. These extra connections are called "bypass tracts" or "accessory pathways". Accessory pathways consist of tiny bands of myocardial tissue that most commonly insert in atrial muscle on one end and ventricular muscle on the other end. The most common variety is located along the AV groove.

Accessory pathways offer a potential parallel route for electrical impulses, bypassing the normal AV conduction system.

The accessory pathways do not slow down the electrical impulse, like the AV node does. Instead, the accessory pathways conduct impulses more quickly, like myocardial tissue. When they conduct the impulses in the antegrade direction (i.e., from the atria to the ventricles), they precede the normal impulse from AV node, causing premature stimulation and contraction of the ventricles. When they conduct the impulses in the retrograde direction (i.e., from the ventricles to the atria), the atria contract after the ventricles do. In either case, normal heart rhythm becomes disrupted.

Patients with accessory pathways are susceptible to re-entrant tachycardias involving both the AV node and the accessory pathway. The resultant fast heart rate can be potentially life-threatening. The elevated heart rate can lead to serious hemodynamic compromise. Sudden syncope or hemodynamic collapse can occur.

Accessory pathways are generally invisible to the naked eye. They therefore must be located by their electrophysiologic effects.

Catheter-based techniques have been developed to record accessory pathway activation by mapping the left and right annuli of, respectively, the tricuspid valve and the mitral valve. The techniques map these regions within the heart using sensing electrodes carried by catheters introduced by vascular access into the heart.

These catheter-based techniques have allowed identification of the site of the accessory pathway. Once identified, the pathway can be rendered non-conductive by catheter-based ablation techniques.

However, physicians frequently find it difficult to map and ablate around these annuli, particularly when working on the atrial side. Many complex movements are presently required to map the entire annulus using conventional catheters. Stable and intimate contact between the myocardial tissue and the mapping electrodes are often difficult to achieve.

Furthermore, conventional systems require the use of separate ablating elements. Coordinating the position of the mapping electrodes and the ablating electrodes further compounds the difficulties.

As a result, mapping and ablating of accessory pathways using conventional catheter-based techniques are difficult and time consuming. For these reasons, many attempts at creating curative lesions ultimately fail.

There is a need for catheter-based systems and methods that simplify the procedures for mapping and ablating accessory pathways.

SUMMARY OF THE INVENTION

The invention provides systems and methods for improving catheter-based ablations of accessory pathways.

One aspect of the invention provides a multi-purpose array of electrodes for both sensing electrical events about a selected annulus region of the heart as well as for ablating tissue in the selected region. The electrode array comprises a support body having a generally circular shape that conforms to the circumferential geometry of the selected annulus region. An array of electrodes is positioned in a spaced apart pattern along the support body. Signal wires electrically coupled to the electrodes for conveying, in a first mode of operation signals representing electrical events sensed by the electrodes in the selected annulus region and for conveying, in a second mode of operation, energy to ablate tissue in the selected annulus region.

According to this aspect of the invention, the pattern spaces adjacent electrodes in the array no further apart than twice the length of the largest one of the adjacent electrodes. This spacing provides the capability to apply ablating energy uniformly about the entire selected annulus region without periodic movement of the electrode array. At the same time, the electrode spacing permits use of the same electrodes to sense electrical events in the selected annular region.

The electrode array that embodies this aspect of the invention reduces the time and complexity of a sensing and ablating procedure in the selected annulus region. The electrode array requires less manipulation, while providing better tissue/electrode contact and stability than conventional approaches.

In a preferred embodiment, the electrodes in the array comprise ring electrodes made of electrically conducting material. In one arrangement, the electrically conducting material comprises a metallic element fastened to the support body. In another arrangement, the electrically conducting material comprises a coating applied upon the support body.

Another aspect of the invention provides a system for sensing electrical events about a selected annulus region of the heart and for ablating tissue in the selected region. The system comprises a catheter having a guide body that carries the above described electrode array on its distal end. The signal wires electrically coupled to the electrodes are themselves electrically coupled to a controller.

According to this aspect of the invention, the controller is operative in two modes. In the first mode of operation, the controller conveys signals representing electrical events sensed by the electrodes in the selected annulus region. In the second mode of operation, the controller conveys energy to the electrodes to ablate tissue in the selected annulus region.

The controller also includes a display device that is operative in the first mode for displaying graphic information that represents the time differences between the atrial and ventricular electrogram complexes sensed by bipolar pairs of the electrodes on the selected annulus region.

According to this aspect of the invention, the display device shows the time differences sensed by the electrode array to progressively increase from a minimum amount up to a maximum amount, and then progressively decrease back to the minimum amount. The accessory pathway is located in the region of the electrode where the minimum time difference occurs. The display device thereby points the physician to the location of the accessory pathway.

In a preferred embodiment, the display device shows the time differences as either as alpha-numeric characters, or as colors that change according to the magnitude of the time differences, or both.

The invention provides precise positioning information with respect to an accessory pathway, without requiring the physician to know the absolute location of the array electrodes or of even the accessory pathway itself. According to the invention, the physician can proceed to ablate the accessory pathway without pinpointing its exact coordinates along the annulus.

In a preferred embodiment, the display device also shows electrogram signal morphologies for selected one or more of the bipolar electrode pairs. In this arrangement, each selected electrogram signal morphology is displayed in a color that changes according to the magnitude of the time difference associated with the selected electrogram signal morphology.

Another aspect of the invention provides a method for sensing electrical events about a selected annulus region of the heart. The method establishes a contact site between heart tissue along the selected annulus and an electrode array as generally described above. The method continuously maintains the site of contact between the electrode array and heart tissue while conveying signals representing electrical events sensed by bipolar pairs of electrodes in the selected annulus region. The method displays the signals as graphic information that represents the time differences between the atrial and ventricular electrogram complexes sensed by the bipolar pairs of the electrodes on the selected annulus region. The method selects the bipolar pair of electrodes that displays the least time separation between the atrial and ventricular complex. According to the invention, this electrode pair identifies the region of the accessory pathway.

In a preferred embodiment, the method includes the step of conveying energy to one or more of the electrodes of the selected bipolar pair to ablate tissue in the selected annulus region.

The various aspects of the invention provide systems and methods for locating and ablating accessory pathways about the annulus of either the tricuspid valve or the mitral valve. The ablation destroys the myocardial tissue in those regions where reentry circuits occur. The ablation interrupts electrical conduction in the accessory pathways, preventing tachycardia.

BRIEF DESCRIPTION OF THE DRAWINGS

FIG. 6 is a side section view of a guide sheath used to introduce and deploy the element shown in FIG. 2 within the heart, with the element shown carried within the guide sheath;

FIG. 7 is a side section view of the guide sheath shown in FIG. 6, with the element shown deployed outside the guide sheath;

FIG. 10 is an enlarged view of the correspondence between the mapping display provided by the system shown in FIG. 5 and the electrodes carried by the element shown in FIGS. 2 to 4;

FIG. 11 is a diagrammatic view of a typical electrogram showing the time difference between the atrial complex and the ventricular complex;

FIG. 12 is an enlarged view of a display that embodies features of the invention and its correspondence between the electrodes carried by the element shown in FIGS. 2 to 4;

FIG. 13 is an enlarged view of a display that also embodies the features of the invention and that includes, in addition to a graphic display of sensed time difference, corresponding electrogram recordings;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EBODIMENTS

Figure 1:
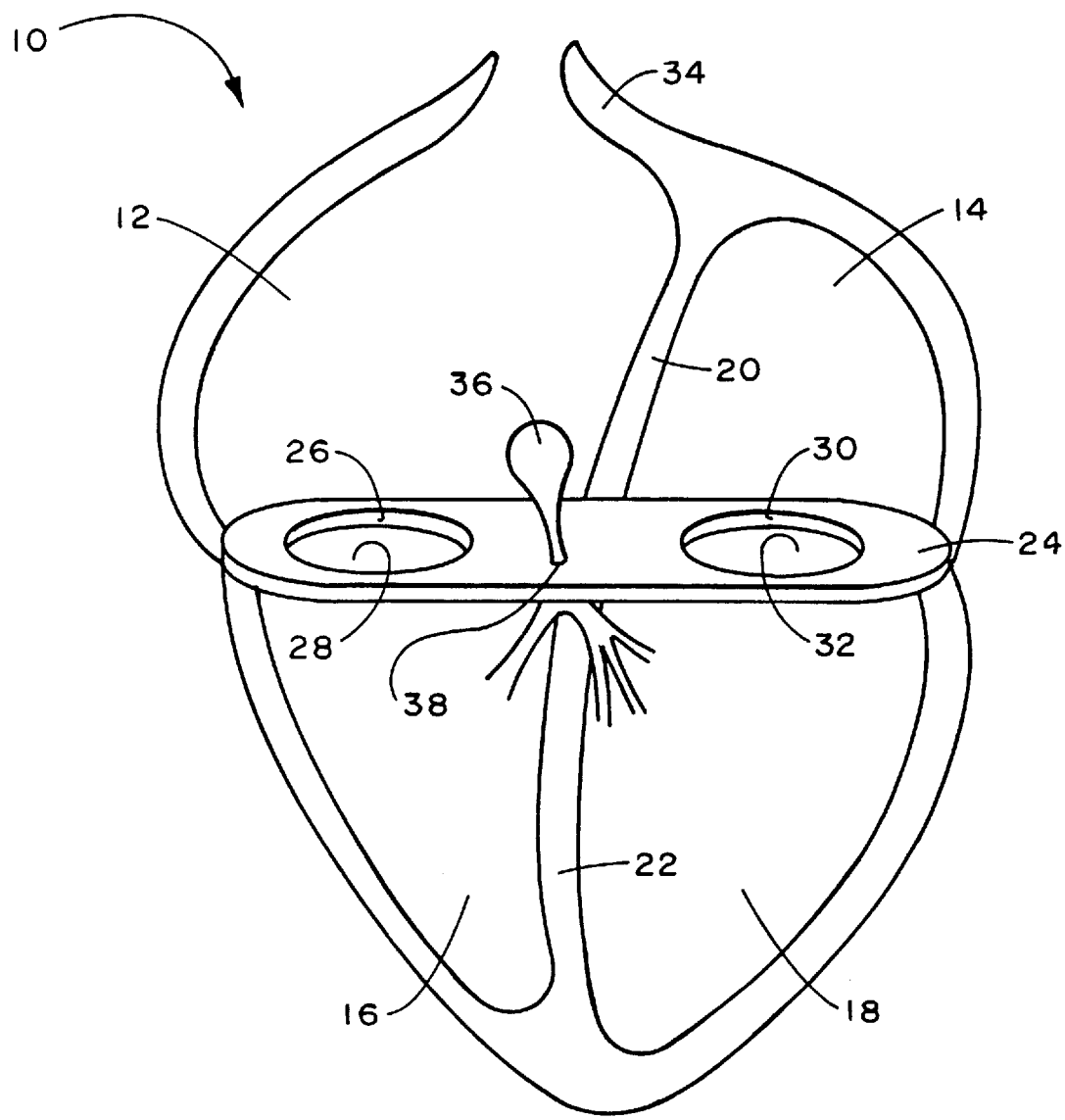
FIG. 1 is a simplified and diagrammatic sectional side view of the interior of the human heart.

FIG. 1 shows a simplified and diagrammatic view of the interior structure of the human heart 10.

The views of the heart 10 shown in FIG. 1 and other Figures in this Specification are not intended to be anatomically accurate in every detail. The Figures show views of the heart 10 in diagrammatic form as necessary to demonstrate the features of the invention.

FIG. 1 shows the right and left right atria, respectively 12 and 14. FIG. 1 also shows the right and left ventricles, respectively 16 and 18.

FIG. 1 further shows the atrial septum 20 that separates the right and left atria 12/14. FIG. 1 also shows the ventricular septum 22 that separates the right and left ventricles 16/18.

FIG. 1 also shows the fibrous structure of the AV groove 24 separating the atria 12/14 from the ventricles 16/18. The ring or annulus 26 of the tricuspid valve 28 is formed in the AV groove 24 between the right atrium 12 and right ventricle 16. The ring or annulus 30 of the mitral (or bicuspid) valve 32 is formed in the AV groove 24 between the left atrium and the left ventricle.

The AV conduction system includes the sinoatrial node (or "SA node") 34, which generates an electrical impulse to begin normal sinus rhythm. In a normal heart, the impulse propagates uniformly across the right and left atria 12/14 and the atrial septum 20 to the atrioventricular (AV) groove 24, causing the atria 12/14 to contract.

As the atria 12/14 contract, blood in the atria 12/14 enters the ventricles 16/18 through the tricuspid and mitral valves 28 and 32.

The AV conduction system further includes the atrioventricular node (or "AV node") 36 and the bundle of HIS (or "HIS bundle") 38, through which the electrical impulse crosses over the AV groove 24 to the ventricles 16/18.

The AV node 36 first slows the conduction of the impulse, allowing the atria 12/14 to completely contract. The HIS bundle 38 then delivers the slowed impulse to the ventricles 16/18, causing them to contract.

Figure 2:
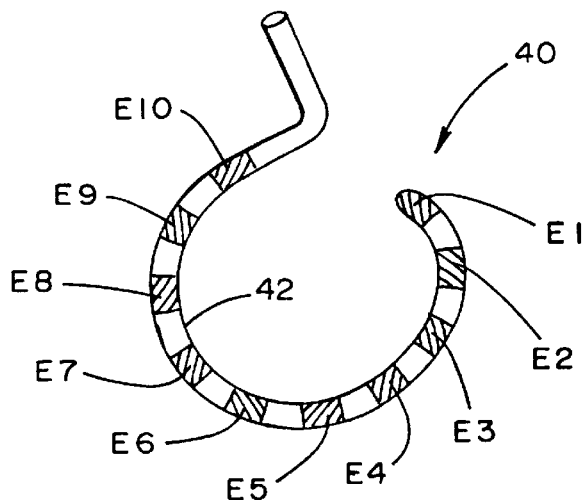
FIG. 2 is a front view of a multi-function element that can be used to both locate and ablate accessory pathways about annuli within the heart.
Figure 3:
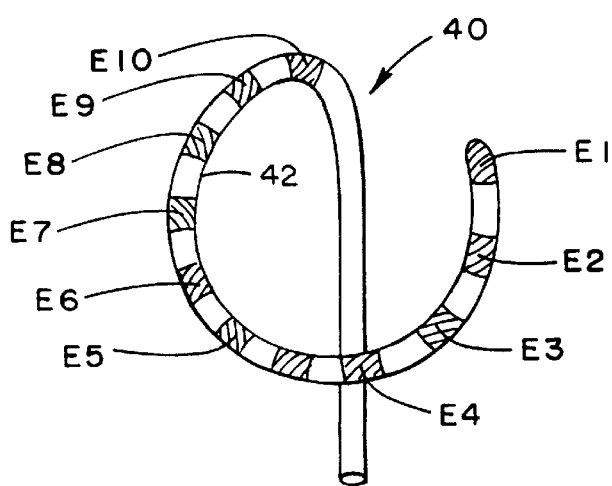
FIG. 3 is a top view of the element shown in FIG. 2.
Figure 4:
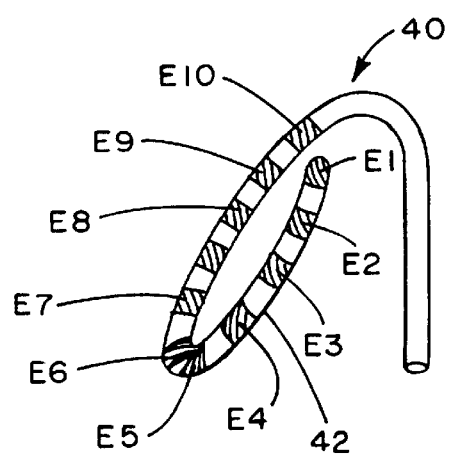
FIG. 4 is a side view of the element shown in FIGS. 2 and 3.

FIGS. 2 to 4 show from various perspectives a multiple function element that locates and ablates accessory pathways about the valve annuli 26/30 on the AV groove 24. FIG. 2 shows the element 40 from the top. FIG. 3 shows the element 40 from the front. FIG. 4 shows the element 40 from the side.

The element 40 comprises an elongated body 42 that is preformed into a generally curved or circular shape, resembling an open loop. The shape corresponds to the circumferential geometry of a selected annulus 26/30.

The body 42 is preferably formed of an electrically nonconductive, biocompatible, resilient plastic material which retains its shape and does not soften significantly at human body temperature, like Pebax®, polyethylene, or Hytral®, (polyester).

The geometry of the body 42 can be created by thermoforming it into the desired shape. Alternatively, the body 42 can include an interior core of super-elastic material, like Nitinol wire, which is itself preshaped into the desired configuration.

This construction provides the body 42 with a modulus the lends both resilience and mechanical strength. As a consequence, the body 42 can be maneuvered by the physician into stable and uniform contact about the selected annulus 26/30.

The preformed shape of the body 42 is selected among a variety of curved geometries to overlie the anatomical geometry of the selected annulus. Since the tricuspid and mitral annuli 26/30 typically possess different geometries, so the invention can provide elements 40 possessing different corresponding shapes.

Regardless of its particular shape, the body 42 carries an array of ring electrodes aligned side by side along the axis of the body 42. Ten electrodes are shown in FIGS. 2 to 4, designated E1 to E10. As FIGS. 2 to 4 show, the electrode array can also include an electrode E1 on the distal tip of the body 42.

The ring electrodes E1 to E10 can be made of a solid, electrically conducting material, like platinum or gold, attached about the body 42. Alternatively, the ring electrodes E1 to E10 can be formed by coating the exterior surface of the body 42 with an electrically conducting material, like platinum or gold. The coating can be applied using sputtering, ion beam deposition, or equivalent techniques.

The electrodes E1 to E10 are electrically isolated one from the other.

If the electrodes are made from inflexible, metallic materials, they should not exceed 6 mm in length to preserve the overall flexibility of the element 40. If the electrodes are applied by coating, larger electrodes can be used. The spacing between adjacent electrodes should not be more than about twice the length of an individual electrode, so that the electrodes can serve two functions. First, they can uniformly apply ablating energy. Second, they can sense electrical events in heart tissue.

For example, if each electrode is 2 mm in length, they should not be spaced apart by more than 4 mm. Electrodes spaced apart by more than twice their individual length will not apply ablating energy uniformly about the entire annular area, unless the element 40 is periodically moved.

The number of the ring electrodes E1 to E10 in the array can vary. In representative embodiments, the number of electrodes can range from about 6 to about 20. Of course, more or fewer electrodes could be used. The particular spacing between them can vary, depending upon the particular geometry of the region of use and the functionality desired, keeping in mind the minimum spacing requirements described above.

According to the invention, because of their close spacing, the ring electrodes E1 to E10 serve two functions. In one mode, the electrodes E1 to E10 serve as sensing or mapping electrodes to monitor the electrical activity in the AV groove about a selected annulus 26/30. In another mode, the electrodes E1 to E10 serve as ablation electrodes to emit energy to ablate tissue about the selected annulus 26/30.

According to the invention, the element 40 is part of an overall system 46 (see FIG. 5) that delivers, deploys, and operates the element 40 inside the heart.

Figure 5:
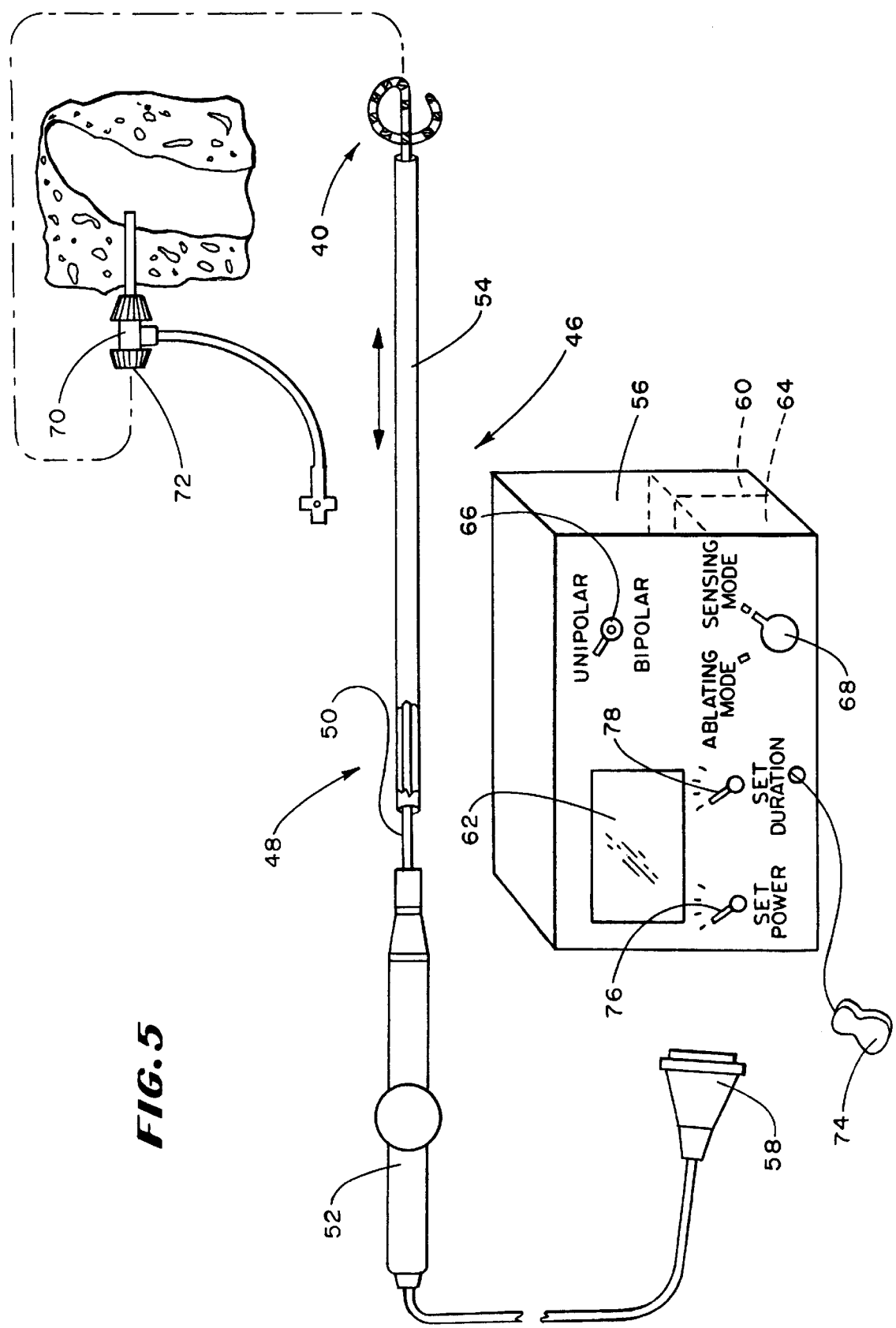
FIG. 5 is a view of a system for mapping and ablating annuli of the heart using the element shown in FIGS. 2 to 4.

As FIG. 5 shows, the system 46 includes a probe 48. The probe 48 has a guide tube 50 that carries the element 40 at its distal end. The probe 48 also includes a handle or grip 52 attached to the proximal end of the guide tube 50. The guide tube 50 carries a guide sheath 54, which slides fore and aft along the axis of the guide tube 50.

As FIG. 6 shows, sliding the guide sheath 54 forward (that is, toward the element 40), progressive straightens out the resilient body 42, drawing it into the guide sheath 54.

Confined within the guide sheath 54, the body 42 assumes the generally linear, low profile shape of the guide sheath (as FIG. 6 shows). The low profile shape allows the physician to employ conventional percutaneous access techniques to introduce the element 40 into a selected region of the heart through a vein or artery.

As FIG. 7 shows, sliding the guide sheath 54 to the rear (that is, away from the element 40), frees the body 42 from the confines of the sheath 54. The resilient memory of the body 42 causes it to return to its preformed shape (as FIG. 7 shows).

As FIG. 5 shows, the system 46 also includes a controller. Each ring electrode E1 to E10 is electrically coupled to a signal wire (not shown) made of an electrically conductive material, like copper alloy. The signal wires extend through the guide tube 50 into the handle 52. One or more connectors 58 attach the proximal ends of the signal wires to an input plug on the controller 56.

The controller 56 includes a signal monitor module 60. The signal monitor module 60 receives electrical signals detected by the ring electrodes E1 to E1. The signal monitor module 60 processes the electrical signals to assist the physician in locating the site of accessory pathway relative to the selected annulus 26/30.

In the illustrated and preferred embodiment (see FIG. 5), the signal monitor module drives a display device 62 on the controller 56. The display device 62 presents an analysis of electrical activity in a format that the physician can readily view and interpret.

The controller 56 also includes a generator module 64 that creates and transmits ablating energy to a selected one or more of the ring electrodes E1 to E10. The selected ring electrodes E1 to E10 emit the energy to ablate myocardial tissue they are in contact with.

While the particular type of ablating energy can vary, the illustrated embodiment, the generator module 64 transmits radiofrequency electromagnetic energy to the selected electrodes E1 to E10.

Preferably, the generator module 64 can be operated (through the switch 66) to apply ablating energy to the ring electrodes E1 to E10 in either a unipolar mode or a bipolar mode (as FIG. 5 shows).

The controller also includes a switch 68 for selecting either the signal monitor module 60 or the energy generator module 64, thereby choosing between operating the electrodes in a SENSING MODE and an ABLATING MODE (as FIG. 5 shows).

To introduce and deploy the element 40 within the heart, the physician uses a conventional introducer 70 (see FIG. 5) to establish access to a selected vein or artery.

With the guide sheath 54 moved forward and enclosing the element 40 (as FIG. 6 shows), the physician introduces the guide tube 50 and outer sheath 54 through a conventional hemostatic valve 72 on the introducer 70 (see FIG. 5). The physician progressively advances the guide tube 50 and guide sheath 54 through the access vein into the right atrium 12.

The physician observes the progress of the guide sheath 54 using fluoroscopic or ultrasound imaging, or the like. The guide sheath 54 can include a radio-opaque compound, such as barium, for this purpose. Alternatively, a radio-opaque marker can be placed at the distal end of the guide sheath 54.

The guide sheath 54 can itself be preshaped with a memory that assumes a prescribed curvature for simplifying access to the right or left atrium 12/14 through venous access.

In an alternative embodiment (not shown), the probe 48 can incorporate conventional catheter steering technology. This would provide the capability of remotely steering the element 40 during introduction into and use within the heart. once located in the desired atrium 12/14, the physician slides the guide sheath 54 back to free the element 40 (as FIG. 7 shows). The element 40 resiliently springs into its curved shape.

The physician can use fluoroscopic or ultrasound imaging, or the like, to observe the element 40 while maneuvering it into contact with the selected annulus 26/30. Alternatively, the physician can deploy an angioscopic or ultrasonic viewing probe to aid positioning.

Figure 8:
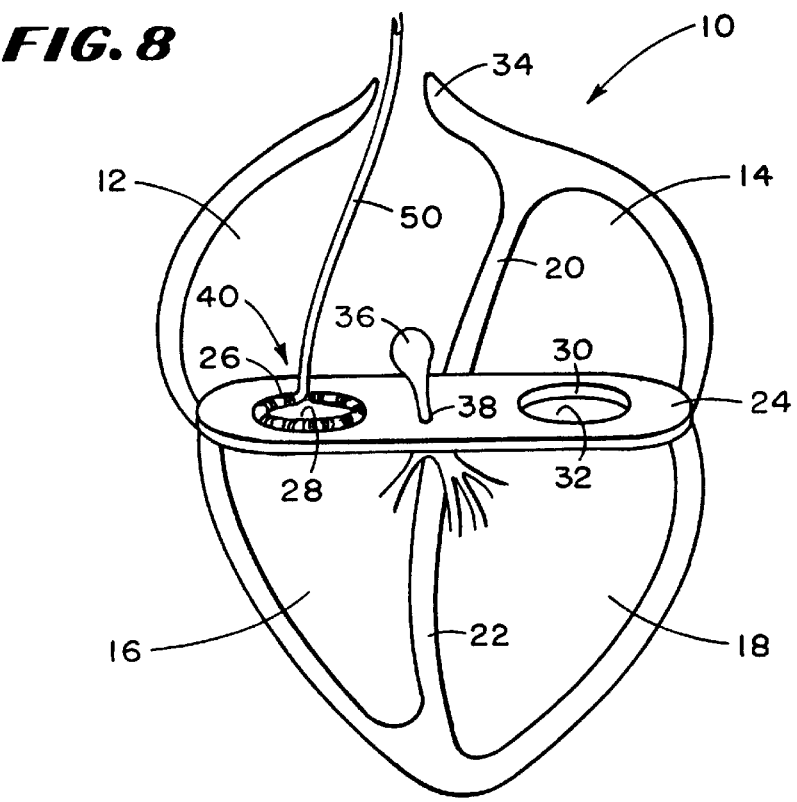
FIG. 8 is a diagrammatic view of the element shown in FIGS. 2 to 4 deployed on the annulus of the tricuspid valve in the right atrium.

Using the invention, access to the annulus 26 of the tricuspid valve 28 can be accomplished through either the subclavian or jugular veins, without the need to remotely steer the element 40. FIG. 8 shows the element 40 in contact with the annulus 26 of the tricuspid valve 28 in the right atrium 12.

Figure 9:
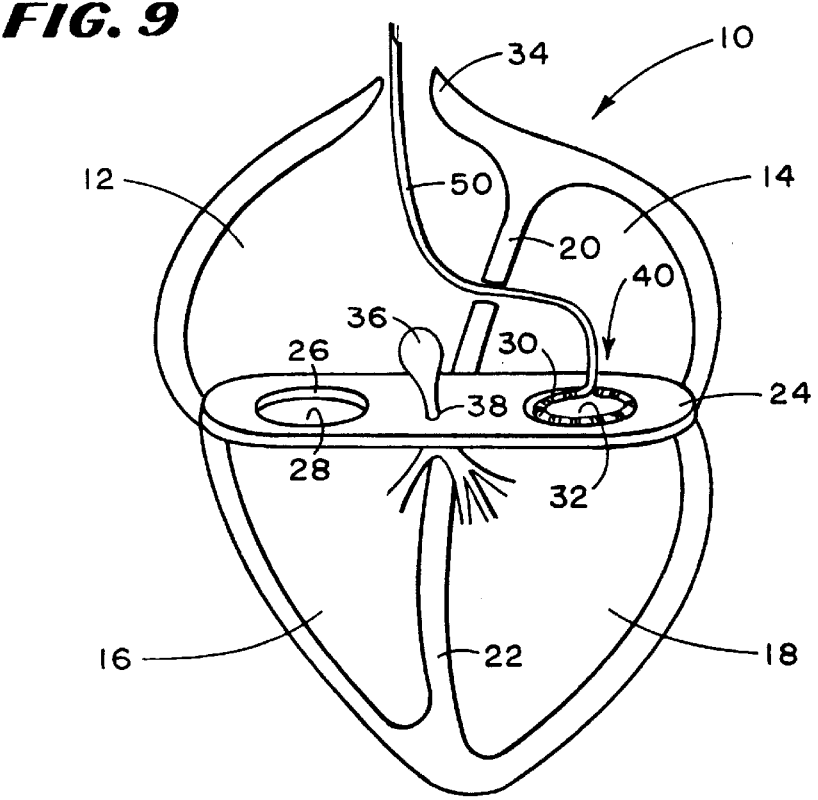
FIG. 9 is a diagrammatic view of the element shown in FIGS. 2 to 4 deployed on the annulus of the mitral valve in the left atrium.

Using the invention, access to the annulus 30 of the mitral valve 32 can also be accomplished through either the subclavian or jugular veins, employing a transeptal approach. Using this approach, the physician enters the left atrium 14 from the right atrium 12 through the atrial septum 20. This approach is a well known and widely accepted technique used in other left atrium access procedures. FIG. 9 shows the element 40 in contact with the annulus 30 of the mitral valve 32 in the left atrium 14 after completion of a transeptal approach.

As FIGS. 8 and 9 show, the element 40 is preferably placed in contact against the selected annulus 26/30 from the atrial side. Alternatively, the element 40 could be placed in contact underneath (i.e., on the ventricular side) the associated valve, resting against the annulus 26/30 behind the chordae tendineae. The geometry required for a ventricular placement will generally differ from that suited for an atrial-placement. The placement would depend upon the physician's choice and whether the insertion point of the accessory pathway is believed to lie on the atrial or ventricular side of the selected annulus 26/30.

Once the physician obtains good contact between the electrodes E1 to E10 and the selected annulus 26/30, the physician takes steps to map the electrical events in the annulus 26/30.

Operating the switch 68 on the controller 56, the physician selects SENSING MODE. This activates the signal monitor module 60 and its associated display 62.

The signal monitor module 60 receives signals from the electrodes E1 to E10. These signals record electrical events in the cardiac cycle. The signal monitor module 60 analyses the signals and converts them to graphic images on the display 62. The signal monitor module 60 can include a conventional microprocessor (e.g., using a 386/486 motherboard) to analyze and convert the signals.

The nature and character of the graphic images on the display 62 can vary. In the illustrated and preferred embodiment (as FIG. 10 shows), the display presents an array of graphic characters or icons, equal in number to the number of electrodes carried on the element.

In the illustrated display, the graphic characters take the shape of boxes (designated BOX1 to BOX10 in FIG. 10). The boxes are numbered to correspond to positions of bipolar pairs of the electrodes, as counted from the distal tip of the element 40. In the illustrated embodiment, there are ten electrodes E1 to E10 on the element, so there are ten numbered boxes BOX1 to BOX10 presented on the display 62. A display 62 can be presented on a conventional CRT screen. Alternatively, the display can presented on an LCD screen, or as a series of small lights or LCD's.

Preferably, the controller 56 includes an input device 74 for entering commands (see FIG. 5).

In the illustrated embodiment, the input device 74 is a conventional mouse, and the display 62 incorporates an interface that receives mouse-driven input. Alternatively, the display 62 can integrate input and output by incorporating conventional touch screen technology. Other conventional input devices can also be used, like a key board or a voice activated input.

According to another aspect of the invention, the individual boxes BOX1 to BOX10 display graphic information that represents the time difference between the atrial and ventricular electrogram complexes sensed by the bipolar pairs of ring electrodes E1 to E10 about the selected annulus 26/30.

As FIG. 10 shows, BOX1 displays the information associated with the complex recorded between electrodes E1 and E10. BOX2 displays the information associated with the complex recorded between electrodes E1 and E2. BOX3 displays the information associated with the complex recorded between electrodes E2 and E3. BOX4 displays the information associated with the complex recorded between electrodes E3 and E4. BOX5 displays the information associated with the complex recorded between electrodes E4 and E5. BOX6 displays the information associated with the complex recorded between electrodes E5 and E6. BOX7 displays the information associated with the complex recorded between electrodes E6 and E7. BOX8 displays the information associated with the complex recorded between electrodes E7 and E8. BOX9 displays the information associated with the complex recorded between electrodes E8 and E9. BOX10 displays the information associated with the complex recorded between electrodes E9 and E10.

FIG. 11 shows the time difference in a typical electrogram as the time between the initiation of the atrial complex A (identified as T1) and the initiation of the ventricular complex V (identified as T2). The time difference (T2 − T1) is displayed either in absolute terms, as a number, or in symbolic terms, as colors within the boxes BOX1 to BOX10, or both.

FIG. 12 shows the element 40 in position on the atrial side of the tricuspid annulus 26, as well as the associated display 62.

The location of an accessory pathway is shown in FIG. 12 to appear on the annulus 26 at site AP. According to the invention, the sensed time difference between the atrial and ventricular complexes present by the display 62 will be the smallest where the accessory pathway AP is located.

Electrode E3 lies closest to site AP. As the display 62 shows in FIG. 12, the time difference in BOX3 (as measured between electrodes E2 and E3) to the smallest at 50 msec. The time difference progressively increases with distance from the accessory pathway AP up to a maximum time difference (150msec) at a location diametrically spaced across the annulus 26 from the accessory pathway AP (at BOX8, as measured between electrodes E7 and E8).

Alternatively, or in addition to, the signal monitor module 60 can also display a selected first color (C1) in the box (i.e., BOX3) corresponding to the smallest time difference. The display 62 progressively varies the colors or shades of color C2 to C6 in the other BOXES to correspond with the progressively increasing time differences.

For example, the sensing system can cause the smallest time difference to display the color red as C1. The subsequent colors C2 to C5 sequentially fade using different colors (or different shades of the same color) from red to yellow and eventually to blue (as C6).

In this way, the display 62 shows the progression of the time differences along the accessory pathway. This helps the physician interpret the output with a glance.

In the illustrated and preferred embodiment (see FIG. 13), the display 62 also includes the capability to display electrogram recordings 83 made by electrode pairs about the annulus 26, as selected by the physician based upon the time difference analysis. FIG. 13 shows the selected pairs to be E1/E10; E2/E3; E4/E5; and E7/E8 (that is, BOX1; BOX3; BOX5; and BOX8). The electrogram signals 83(1); 83(3); 83(5); and 83(8) can also be displayed in the same colors according to the time difference color code, as FIG. 13 shows.

By showing selected electrogram signal morphologies 83(1)/(3)/(5)/(8), the display 62 can be used to confirm the results of the time difference analysis. The electrogram signal morphology can be used by the physician to confirm the identity of the region of the accessory pathway AP. For example, in FIG. 13, the electrogram signal 83(3) (selected as the site of the accessory pathway AP by the time difference analysis) also shows the shortest time between complexes), further indicating close proximity to the accessory pathway AP.

Electrogram morphology also can be used by the physician to confirm uniform contact between the element 40 and the annulus 26. The electrogram morphology can also be used to confirm the presence of an underlying valve structure (as would occur along the mitral valve annulus 30 close to the ventricular septum 22), where only low amplitude far-field signals are sensed.

With the display 62, the physician does not have to know the absolute location of the ring electrodes or insertion point of the accessory pathway itself. With the display 62, the physician knows that it is somewhere along the annulus. The invention allows the physician to proceed to ablate the insertion point without pinpointing its exact coordinates along the annulus.

The display shown in FIG. 13 suggests that the insertion point of the accessory pathway is somewhere in the region of electrode E3.

With this information, the physician takes steps to ablate the insertion point. Operating the switch 68, the physician selects ABLATING MODE on the controller 56. This readies the energy generator module 64. The physician can then, upon additional commands, supply ablation energy to the element 40.

Using the input device 74, the physician selects one or more electrodes E1 to E10 on the element 40 for receiving ablating energy.

When the input device 74 is mouse-driven, the physician operates the mouse to click-on the box or boxes BOX1 to BOX10 corresponding to electrodes E1 to E10 the physician wants to receive ablating energy. When the input device is a touch screen, the physician touches the box or boxes on the screen corresponding to the electrode or electrodes the physician wants to receive ablating energy. When the input device is a key board, the physician types in the electrode numbers. When the input device is composed of multiple push buttons, the physician pushes the buttons corresponding to the selected electrodes or electrode pairs.

The particular electrode selection and activation scheme depends upon whether the controller is operating in the unipolar or bipolar mode, as controlled by the switch 66.

If the system is operating in a unipolar mode, the physician selects one or more electrodes in the region of the identified insertion point. Based upon the display shown in FIG. 12, the physician would have the option of selecting electrode E3 alone, or electrodes E3 and E4; or electrodes E2 and E3; or electrodes E2, E3, and E4.

The energy generator module 64 supplies power to the selected electrode or electrodes, based upon previously established ablation parameters (power, duration, etc., set by other switches 76 and 78 on the controller 56).

The energy transmitted by the electrode(s) flows to an external indifferent electrode on the patient (not shown), which is typically an epidermal patch. The energy creates a region of thermally destroyed tissue (the lesion) where the tissue contacts the energized electrode(s).

If the controller 56 is operating in a bipolar mode, the physician has the option of selecting two or more adjacent electrodes in the region of the identified insertion point. For example, based upon the display in FIG. 12, the physician can select electrodes E2 and E3; or electrodes E2, E3, and E4; or electrodes E3 and E4.

The energy generator module 64 sets the polarity of selected electrodes to deliver a bipolar lesion between the designated electrodes.

In the bipolar mode, the element can be operated with higher impedance, higher efficiencies, and more sensitivity to tissue contact than when operated in the unipolar mode.

Using the switch 68, the physician can successively toggle between the SENSING MODE and the ABLATING MODE until the elimination of the accessory pathway has been confirmed.

The physician then slides the guide sheath 54 forward to enclose the element 40. The physician then withdraws the guide tube 50 and guide sheath 54 from the heart, ending the procedure.

In an alternative embodiment (shown in FIG. 14), the element 40 is carried at the distal end of a probe 80 which, unlike the probe 48 shown in FIG. 5, does not include a guide sheath 54 to control the shape of the element 40. Instead, the probe 80 includes a conventional steering mechanism 82 with an external steering lever 84 for selectively bending or flexing the element 40 along its length, as the solid and phantom lines in FIG. 14 show.

A representative steering mechanism 82 that can be used is shown in Copending U.S. Application Ser. No. 07/789, 260, now U.S. Pat. No. 5,365,861 which is incorporated by reference.

Figure 14:
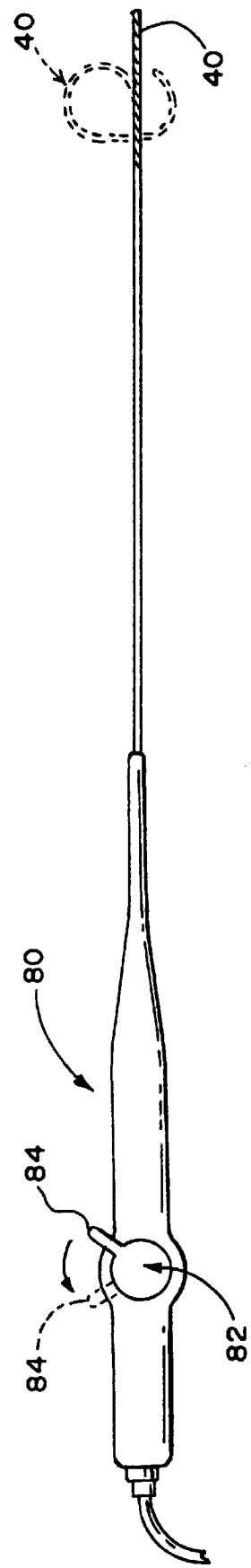
FIG. 14 is an alternative embodiment of a probe that carries the element shown in FIGS. 2 to 4 and that shapes the element without using an outer guide sheath.

As FIG. 14 shows in solid lines, forward movement of the steering lever 84 straightens the element 40. As FIG. 14 shows in phantom lines, rearward movement of the steering lever 84 flexes or curves the element 40 into its desired loop shape.

Other alternative embodiments of the element would also not require a guide sheath 54. One alternative embodiment (not shown) includes the use of "shape memory" material that would change the shape of the element upon exposure to the temperature conditions present in the heart. Another alternative embodiment would include an internal sliding stylet to shape the element, as disclosed in copending patent Application Ser. No. 08/099,843, filed Jul. 30, 1993, entitled "Variable Curve Electrophysiological Catheter," now U.S. Pat. No. 5,397,321, and copending patent application Ser. No. 08/100,739, filed Jul. 30, 1993, entitled "Variable Stiffness Electrophysiological Catheter," now abandoned.

In still another alternative embodiment, the element itself may possess sufficient inherent flexible to permit its advancement through the vasculature with an outer sheath.

Nevertheless, use of the sliding guide sheath 54 to control the shape of the element 40 (as FIGS. 6 and 7 show) is still preferred, because it allows the element 40 to inherently possess greater stiffness to generate greater contact forces about the selected annulus than the alternative embodiments would permit.

According to the invention, the selected annulus 26/30 can be mapped and ablating at one time, without the need to continuously reposition the element 40 and without the need to employ a separate ablation probe. The invention results in better tissue/electrode contact and stability, to minimize the occurrence of ineffective applications of ablating energy. The invention thereby provides shorter and more effective procedures, with greater incidence of curative lesions.

The features of the invention are set forth in the following claims.

We claim:

1. A system for sensing electrical events about a selected annulus region of the heart and for ablating tissue in the selected region comprising a catheter comprising
      a guide body having a distal end and a proximal end,
      a handle carried on the proximal end of the guide body for manipulating the guide body,
   an electrode array carried on the distal end of the guide body for sensing electrical events in heart tissue including
      a support body having a generally circular shape that conforms to the circumferential geometry of the selected annulus region,
      an array of electrodes positioned in a spaced apart pattern along the support body,
   signal wires electrically coupled to the electrodes
   a controller electrically coupled to the signal wires and being operative
      (i) in a first mode of operation for conveying signals representing electrical events sensed by bipolar pairs of the electrodes in the selected annulus region, and
      (ii) in a second mode of operation for conveying energy to one or more of the electrodes to ablate tissue in the selected annulus region, and
   the controller further including means for switching between the first and second modes of operation and display means, operative in the first mode, for displaying graphic information that represents the time differences between the atrial and ventricular electrogram complexes sensed by the bipolar pairs of the electrodes on the selected annulus region.

2. A system according to claim 1 wherein the display means shows the time differences as alpha-numeric characters.

3. A system according to claim 1 wherein the display means shows the time differences as colors that change according to the magnitude of the time differences.

4. A system according to claim 1 wherein the display means shows electrogram signal morphologies for selected one or more of the bipolar electrode pairs.

5. A system according to claim 4 wherein each selected electrogram signal morphology is displayed in a color that changes according to the magnitude of the time difference associated with the selected electrogram signal morphology.

6. A system according to claim 1 wherein the pattern spaces adjacent electrodes in the array no further apart than twice the length of the largest one of the adjacent electrodes.

* * * * *